: US 11,491,080 B2
(45) Date of Patent: Nov. 8, 2022

(12) United States Patent
Chao

(54) SYSTEM FOR GENERATING STIMULATIONS IN RELATION TO MEDICINES, AND MERIDIANS, ORGANS AND TISSUES OF A HUMAN BODY

(71) Applicant: Kuang-Cheng Chao, New Taipei (TW)

(72) Inventor: Kuang-Cheng Chao, New Taipei (TW)

(*) Notice: Subject to any disclaimer, the term of this patent is extended or adjusted under 35 U.S.C. 154(b) by 389 days.

(21) Appl. No.: 16/808,224

(22) Filed: Mar. 3, 2020

(65) Prior Publication Data
US 2020/0281813 A1 Sep. 10, 2020

(30) Foreign Application Priority Data

Mar. 5, 2019 (TW) .................................. 108107318

(51) Int. Cl.
*A61H 23/00* (2006.01)
*A61H 39/00* (2006.01)
*A61N 1/36* (2006.01)
*A61N 5/06* (2006.01)

(52) U.S. Cl.
CPC ........... *A61H 39/002* (2013.01); *A61H 23/00* (2013.01); *A61H 39/007* (2013.01); *A61N 1/36021* (2013.01); *A61N 5/0619* (2013.01); *A61H 2230/255* (2013.01)

(58) Field of Classification Search
CPC ................................ A61N 1/0002; A61N 1/00
USPC ................................................................. 607/3
See application file for complete search history.

*Primary Examiner* — Nadia A Mahmood
(74) *Attorney, Agent, or Firm* — Hamre, Schumann, Mueller & Larson, P.C.

(57) ABSTRACT

A system for generating stimulations in relation to medicines, and meridians, organs and tissues of a human body includes a control device, a pulse examining device and a stimulation device. Based on a pulsation signal obtained from a user, the stimulation device obtains a meridian-related spectrum. Based on operation input to the control device, the stimulation device obtains an organ-tissue-related spectrum and a medication-related spectrum. The stimulation device obtains a stimulation spectrum by making a linear combination of these spectrums, and stimulates a sensory system of the user based on the stimulation spectrum.

9 Claims, 5 Drawing Sheets

| Options for Meridian | Options for Chinese Medicine |
|---|---|
| ◀ ▶<br>[Spleen Meridian of Foot Taiyin]<br>Intensity<br>◀ ○○○○●●● ▶ | ◀ ▶<br>[Single-drug]<br>Intensity<br>◀ ○○○○●●● ▶<br>◀ ▶<br>[Multiple-drug]<br>Intensity<br>◀ ○○○○●●●● ▶ |
| Options for Organ | Options for Western Medicine |
| ◀ ▶<br>[Spleen]<br>Intensity<br>◀ ○○○○○●●● ▶ | ◀ ▶<br>[Single-drug]<br>Intensity<br>◀ ○○○○○●●● ▶<br>◀ ▶<br>[Multiple-drug]<br>Intensity<br>◀ ○○○○○○○ ▶ |
| Options for Tissue | Options for Frequency |
| ◀ ▶<br>[Muscle]<br>Intensity<br>◀ ○○○○○●● ▶ | ◀ ▶<br>[A.5Hz]<br>Intensity<br>◀ ○○○○○○○ ▶ |

Pulse Examination Message : X X X X X
Suggestion Message : X X X X X

FIG.3

SYSTEM FOR GENERATING STIMULATIONS IN RELATION TO MEDICINES, AND MERIDIANS, ORGANS AND TISSUES OF A HUMAN BODY

CROSS-REFERENCE TO RELATED APPLICATION

This application claims priority of Taiwanese Invention Patent Application No. 108107318, filed on Mar. 5, 2019.

FIELD

The disclosure relates to a stimulation system, and more particularly to a stimulation system that can generate stimulations related to medicines, and meridians, organs and tissues of a human body.

BACKGROUND

In information medicine and quantum medicine, information, frequency and energy are linked to the meridian concept in traditional Chinese medicine. Many theories consider that a human body has three major loop systems: circulation system, nervous system and meridian system, which respectively correspond to mass, energy, and message of a substance. In other words, the circulation system transmits the mass of the substance, the nervous system transmits the energy of the substance, and the meridian system transmits the messages of the substance. Such concept is similar or analogous to the characteristics of waves in physics.

Some treatments in traditional Chinese medicine, such as acupuncture, massage therapy, etc., and electrotherapy that uses electric current to stimulate the meridians or acupoints of the human body all employ the concept of resonance. Vibration or stimulation of a single frequency may induce a resonant effect within the human body, so as to alleviate pain or treat diseases.

However, instead of a single frequency, the meridians of the human body may correspond to multiple different frequencies, so using a wave of a single frequency to perform stimulation may not be the best approach.

SUMMARY

Since meridians may carry holographic (meaning thorough, extensive) information on specific organs, a composite wave, of which a spectrum is a combination of multiple frequencies, or a frequency-varying wave may be more appropriate for stimulating the human body. In addition, Chinese medicines, western medicines, mineral substances, decoctions of Chinese medicines, each correspond to a specific spectrum that may induce a resonant effect on the human body.

Therefore, an object of the disclosure is to provide a system for generating stimulations in relation to medicines, and meridians, organs and tissues of a human body.

According to the disclosure, the system includes a control device, a pulse examining device, and a stimulation device. The control device includes a user interface configured to receive an operation input related to medicines, and meridians, organs and tissues of a human body, and a control module configured to output a control signal based on the operation input. The pulse examining device is configured to output a pulsation signal that is related to arterial pulsation of a user. The stimulation device includes a pulse generator and a stimulator. The pulse generator is coupled to the control module and receiving the control signal therefrom, and is coupled to the pulse examining device and receiving the pulsation signal therefrom. The stimulation device is configured: i) to obtain a fundamental frequency for arteries of the user based on the pulsation signal; ii) to obtain, based on the control signal, a meridian-related spectrum of a single frequency that corresponds to meridians of a human body and that is a harmonic frequency of the fundamental frequency; iii) to obtain, based on the control signal, an organ-tissue-related spectrum of a single frequency that corresponds to organs and tissues of a human body; iv) to obtain, based on the control signal, a medication-related spectrum that corresponds to medicines; v) to generate a stimulation spectrum by making a linear combination of the meridian-related spectrum, the organ-tissue-related spectrum and the medication-related spectrum; and vi) to output a stimulation signal that is related to the stimulation spectrum. The stimulator is coupled to the pulse generator and receives the stimulation signal therefrom, and is configured to stimulate a sensory system of the user based on the stimulation spectrum.

BRIEF DESCRIPTION OF THE DRAWINGS

Other features and advantages of the disclosure will become apparent in the following detailed description of the embodiment(s) with reference to the accompanying drawings, of which:

FIG. 3 is a schematic diagram illustrating exemplary content displayed by a user interface according to the disclosure.

DETAILED DESCRIPTION

Figure 1:
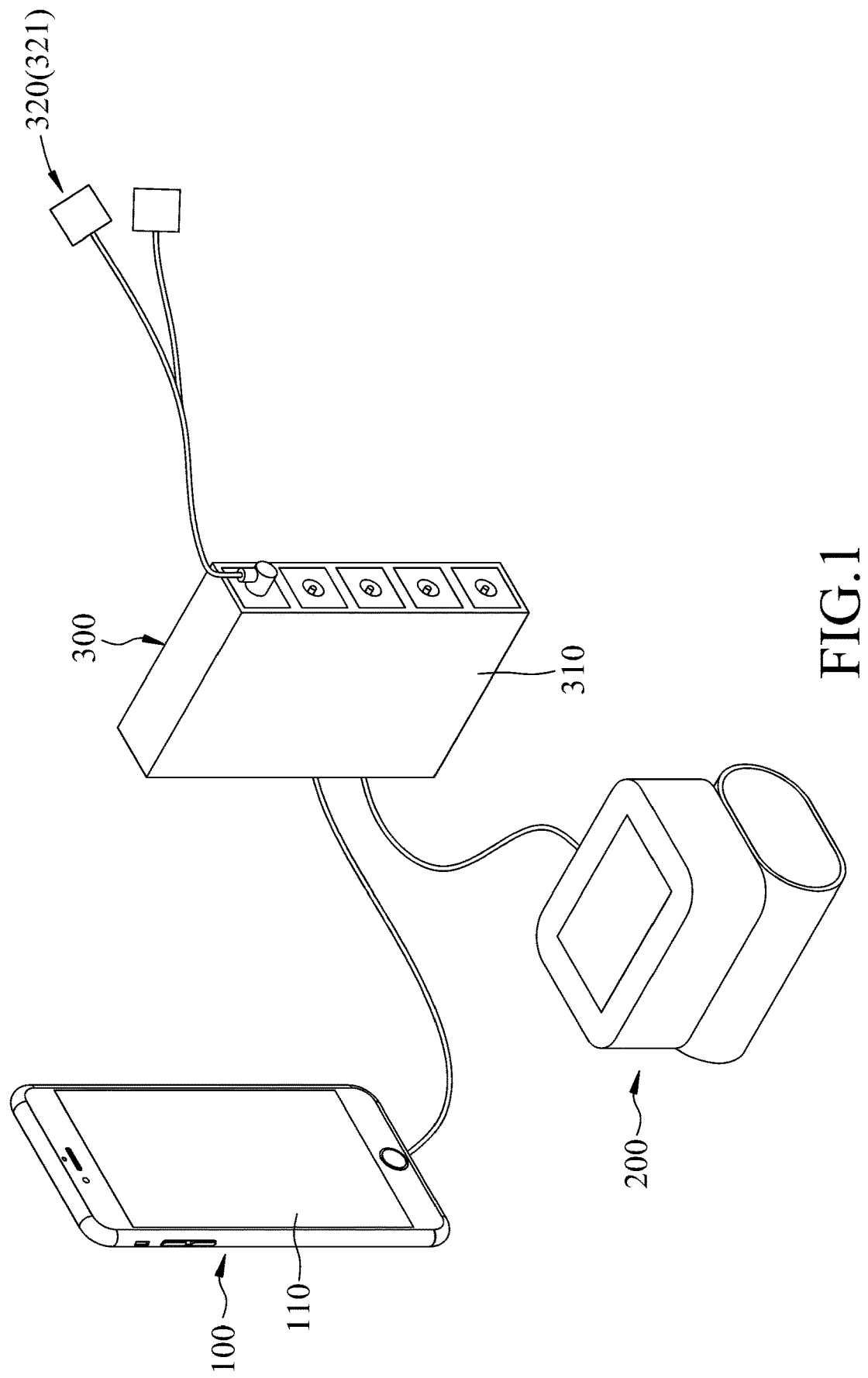
FIG. 1 is a perspective view illustrating an embodiment of a system according to the disclosure, wherein the system is for generating stimulations in relation to medicines, and meridians, organs and tissues of a human body.

Before the disclosure is described in greater detail, it should be noted that where considered appropriate, reference numerals or terminal portions of reference numerals have been repeated among the figures to indicate corresponding or analogous elements, which may optionally have similar characteristics.

Figure 2A:
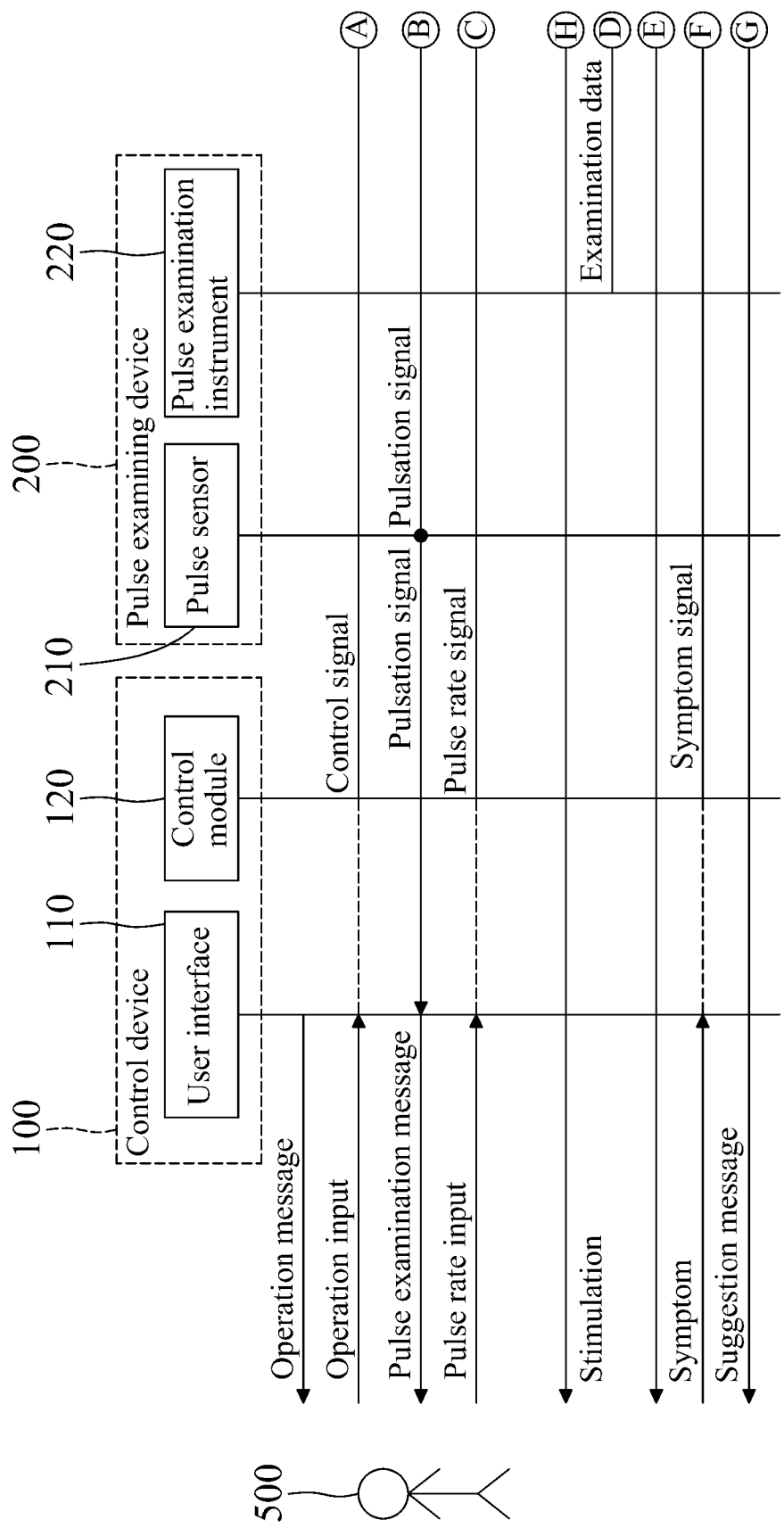
FIGS. 2A and 2B form a schematic diagram illustrating signal transmission of the embodiment.
Figure 2B:
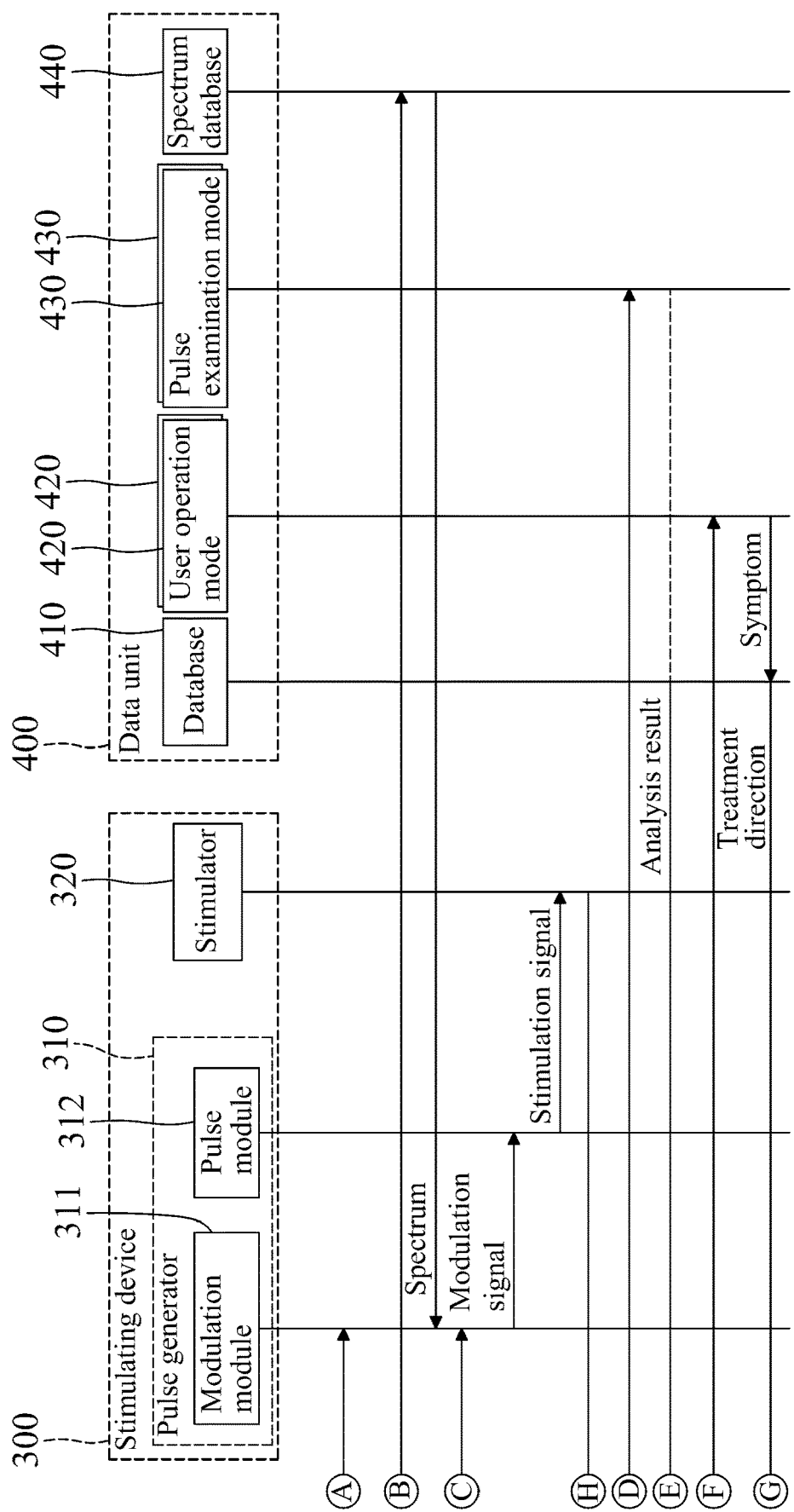

Referring to FIGS. 1, 2A and 2B, an embodiment of a system according to this disclosure is adapted for generating stimulations in relation to medicines, and meridians, organs and tissues of a human body. The system includes a control device 100, a pulse examining device 200, a stimulation device 300 and a data unit 400.

The control device 100 includes a user interface 110 and a control module 120. In this embodiment, the control device 100, the pulse examining device 200, and the stimulating device 300 are communicatively coupled to each other, and the data unit 400 is communicatively coupled to the control device 100 and the pulse examining device 200, but this disclosure is not limited thereto. Further referring to FIG. 3, the user interface 110 is configured to display operation settings, a pulse examination message, and a suggestion message. The operation settings relate to medication, and meridians, organs and tissues of a human body, and are configured for a user 500 to enter an operation input. After the user interface 110 receives the operation input related to the operation settings, the control module 120 outputs a control signal based on the operation input.

It is noted that the operation settings shown by the user interface 110 is not limited to those shown in FIG. 3, and the visual arrangements or functional options may vary in other embodiments. In this embodiment, each parameter of the operation settings, such as meridian, organ, tissue, medication (including Chinese medicine(s) and/or western medicine(s)), and frequency, is adjustable in terms of intensity of stimulation, so as to provide the user 500 with operational flexibility.

The pulse examining device 200 includes a pulse sensor 210 and a pulse examination instrument 220. Since resonant frequencies of organs are related to the heartbeat frequency, the pulse sensor 210 is used to sense arterial pulsation of the user 500 automatically, and to output to the control device 100 and the stimulating device 300 a pulsation signal that has a pulsation frequency related to the arterial pulsation thus sensed. In this embodiment, the pulse examination message displayed by the user interface 110 indicates a pulse rate (i.e., the pulsation frequency) based on the arterial pulsation sensed by the pulse examining device 200. In this embodiment, when the pulse sensor 210 malfunctions and/or is unable to output the pulsation signal, the user interface 110 may be used to manually enter a pulse rate input that indicates a user-determined pulse rate, and the control module 120 may further output to the stimulating device 300 a pulse rate signal related to the user-determined pulse rate. In such a case, the pulse examination message displayed by the user interface 110 may show the user-determined pulse rate. The pulse examination instrument 220 is configured to perform pulse examination on the user 500, and to output to the data unit 400 a result of the pulse examination thus performed (i.e., a pulse condition of the user 500) for analysis and assessment. Because the pulse examination instrument 220 is not the focus of this disclosure, details thereof are omitted herein for the sake of brevity.

The stimulating device 300 includes a pulse generator 310, and at least one pulse stimulator 320 coupled to the pulse generator 310. The pulse generator 310 includes a modulation module 311 and a pulse module 312. The modulation module 311 is coupled to the control module 120 for receiving therefrom the control signal and the pulse rate signal, is coupled to the pulse examining device 200 for receiving therefrom the pulsation signal, and is configured to output to the pulse module 312 a modulation signal based on the control signal and one of the pulsation signal and the pulse rate signal. Upon receipt of the pulsation signal from the pulse examining device 200, the modulation module 311 analyzes the pulsation signal to acquire therefrom the pulsation frequency, and records the pulsation signal to acquire a pulsation spectrum related to pulsations of the arteries of the user 500 within a time interval. According to a theory of resonant blood circulation proposed by Dr. Wei Kung Wang, each artery has a natural resonant frequency, and organs and acupoints are coupled to and vibrate with corresponding arteries, inducing frequency division. Accordingly, each of the organs and the acupoints has a specific resonant frequency. If the organs that correspond to the same resonant frequency are classified into a group, correspondence between the organs and the meridians can be obtained. In addition, since the heartbeat is the source of energy for all resonance in the human body, the frequency of the heartbeat signal (i.e., the pulsation frequency) is a fundamental frequency of the resonant frequencies of the meridians, and so the resonant frequency of each of the meridians would be a harmonic of the heartbeat signal. Relevant theories and applications have been described in U.S. Pat. No. 10,004,663, and details thereof are omitted herein for the sake of brevity.

Accordingly, the modulation module 311 makes the pulsation frequency of the pulsation signal or the user-determined pulse rate as indicated by the pulse rate signal serve as a fundamental frequency for arteries of the user 500 based on the pulsation signal, and obtains the following from the data unit 4 based on the control signal: a meridian-related spectrum (or wave) of a single frequency that corresponds to meridians of the human body and that is a harmonic frequency of the fundamental frequency; an organ-tissue-related spectrum (or wave) of a single frequency that corresponds to organs and tissues of the human body (the single frequency herein may not correspond to both organs and tissues, and may only correspond to organs or only correspond to tissues); and a medication-related spectrum (or wave) that corresponds to medication. The meridian-related spectrum is related to one or more meridians selected in the field of the operation settings that corresponds to meridians (exemplified as "Options for Meridian" in FIG. 3). The organ-tissue-related spectrum is related to one or more organs and/or tissues selected in the field of the operation settings that corresponds to organs (exemplified as "Options for Organ" in FIG. 3) and the field of the operation settings that corresponds to tissues (exemplified as "Options for Tissue" in FIG. 3). The medication-related spectrum is related to one or more medicine types selected in the fields of the operation settings that corresponds to medication (exemplified as "Options for Chinese Medicine" and "Options for Western Medicine" in FIG. 3). Then, the modulation module 311 generates a stimulation spectrum by making a linear combination of the meridian-related spectrum, the organ-tissue-related spectrum and the medication-related spectrum, and outputs to the pulse module 312 a modulation signal that is related to the stimulation spectrum. The stimulation spectrum may be obtained by:

$$F_S = a_1 \times F_1 + a_2 \times F_2 + a_3 \times F_3$$

where $F_S$ represents the stimulation spectrum, $F_1$, $F_2$, $F_3$ respectively represent the meridian-related spectrum, the organ-tissue-related spectrum and the medication-related spectrum and can be obtained from the data unit 4, and $a_1$, $a_2$, $a_3$ are weighting values obtained from the data unit 4 and respectively correspond to the meridian-related spectrum, the organ-tissue-related spectrum and the medication-related spectrum. Each of the weighting values $a_1$, $a_2$, $a_3$ is related to the intensity selected for the corresponding option(s) in the operation settings (see FIG. 3). It is noted that the above equation does not mean that it is necessary for the acquisition of the stimulation spectrum to be performed in the frequency domain. In practice, the acquisition of the stimulation spectrum can be alternatively performed in the time domain.

Lastly, the pulse module 312 outputs to the stimulator 320 a stimulation signal corresponding to the modulation signal, causing the stimulator 320 to stimulate a sensory system of the user 500 based on the stimulation spectrum.

In this embodiment, the control module 120 uses the pulsation spectrum as feedback data to perform feedback control, and determines, based on the pulsation spectrum, adjustments for the weighting values used in the linear combination of the meridian-related spectrum, the organ-tissue-related spectrum and the medication-related spectrum in a real time manner. The control module 120 then outputs the control signal that indicates the adjustments determined for the weighting values in a real time manner, so as to change the stimulation output by the stimulator 320, putting the user 500 in a desired physiological condition that corresponds to the operation input (namely, the stimulation received by the user 500 induces resonance for specific meridians, organs, and/or tissues of the operation setting as selected by the user 500). A multivariable control design can be used to realize such a feature by making the meridian-related spectrum, the organ-tissue-related spectrum and the medication-related spectrum serve as variables. Since these variables are coupled with each other, mathematic computations are required for decoupling operations. The multivariable control design and the decoupling mathematic computations should be well known to one having ordinary skills in the art and are not a focus of this disclosure, so details thereof are omitted herein for the sake of brevity. In this embodiment, the decoupling results and matrices of the weighting values corresponding to various conditions are acquired in advance, so as to generate a lookup table of the weighting values to be stored in the data unit 400, so the control module 120 can use the lookup table to adjust the weighting values for the meridian-related spectrum, the organ-tissue-related spectrum and the medication-related spectrum in a real time manner.

In addition, after the user 500 has taken medication, time required for the medicine(s) to induce the medicinal effect should be taken into consideration by the control module 120 when determining the stimulation spectrum. In this embodiment, the control module 120 may adjust the weighting values $a_1$, $a_2$, $a_3$ to generate different linear combinations of the meridian-related spectrum, the organ-tissue-related spectrum and the medication-related spectrum as time goes by, especially for the weighting value $a_3$, which corresponds to the medication-related spectrum and should therefore vary with time. The modulation module 311 thus makes, based on the control signal, the stimulation spectrum sequentially correspond to different linear combinations of the meridian-related spectrum, the organ-tissue-related spectrum and the medication-related spectrum respectively in different time intervals, and outputs the modulation signal to the pulse module 312 accordingly, so as to follow the pharmacological property of the medicine(s) to enhance the medicinal effect on the user 500.

In this embodiment, medication is classified into Chinese medicine and Western medicine. Chinese medicine is further classified into single-drug (single medicinal herb) and multiple-drug (multiple medicinal herbs). Western medicine is also further classified into single active ingredient drug (a drug composed of a single active ingredient) and combination drug (a drug composed of multiple active ingredients). Accordingly, the medication-related spectrum can be a linear combination of a first spectrum that corresponds to single-drug Chinese medicine, a second spectrum that corresponds to multiple-drug Chinese medicine, a third spectrum that corresponds to single active ingredient drug Western medicine, and a fourth spectrum that corresponds to combination drug Western medicine, and thus can be obtained according to:

$$F_3 = a_{31} \times F_{31} + a_{32} \times F_{32} + a_{33} \times F_{33} + a_{34} \times F_{34}$$

where $F_{31}$, $F_{32}$, $F_{33}$, $F_{34}$ respectively represent the first, second, third and fourth spectrums and can be obtained from the data unit 400, and $a_{31}$, $a_{32}$, $a_{33}$, $a_{34}$ are weighting values obtained from the data unit 4 and respectively corresponding to the first, second, third and fourth spectrums.

If the user 500 takes different types of medicines at the same time, the control module 120 may generate the control signal that indicates the types of medicines taken by the user 500 based on the operation input, and the modulation module 311 can not only obtain, based on the control signal, different linear combinations of the meridian-related spectrum, the organ-tissue-related spectrum and the medication-related spectrum (i.e., different combinations of the weighting values $a_1$, $a_2$, $a_3$) respectively for different time intervals, but also obtain different medication-related spectrums corresponding to different linear combinations of the first to fourth spectrums (i.e., different combinations of the weighting values $a_{31}$, $a_{32}$, $a_{33}$, $a_{34}$) respectively for different time intervals, so the resultant stimulation in any one interval is directed to only one type of the medicines taken by the user 500, with all types of the medicines taken by the user 500 being accounted for by the different linear combinations of the first to fourth spectrums.

For instance, if the user 500 takes minor bupleurum decoction (belonging to multiple-drug Chinese medicine) and an antacid (belonging to single active ingredient drug Western medicine) at the same time, for generation of the stimulation spectrum of the modulation signal, in the beginning, a spectrum corresponding to minor bupleurum decoction (or more specifically corresponding to multiple-drug Chinese medicine) may be disregarded, while a spectrum corresponding to antacid (or more specifically corresponding to single active ingredient drug Western medicine) is linearly combined with the organ-tissue-related spectrum and the meridian-related spectrum. After a period of time, for generation of the stimulation spectrum of the modulation signal, the spectrum corresponding to minor bupleurum decoction may be linearly combined with the organ-tissue-related spectrum and the meridian-related spectrum, while the spectrum corresponding to antacid is disregarded. Because onset of action is usually shorter for Western medicines in comparison with Chinese medicines, the stimulation is made to be consistent with such a characteristic, thereby enhancing the medicinal effects of the medicines.

It is noted that the stimulator 320 can be realized in various ways. For example, the stimulator 320 can be an electrode pad unit 321 (see FIG. 1), a flashing device (not shown), an acoustic frequency generator (not shown), a vibrator (not shown), or a body shaker (not shown).

Figure 4:
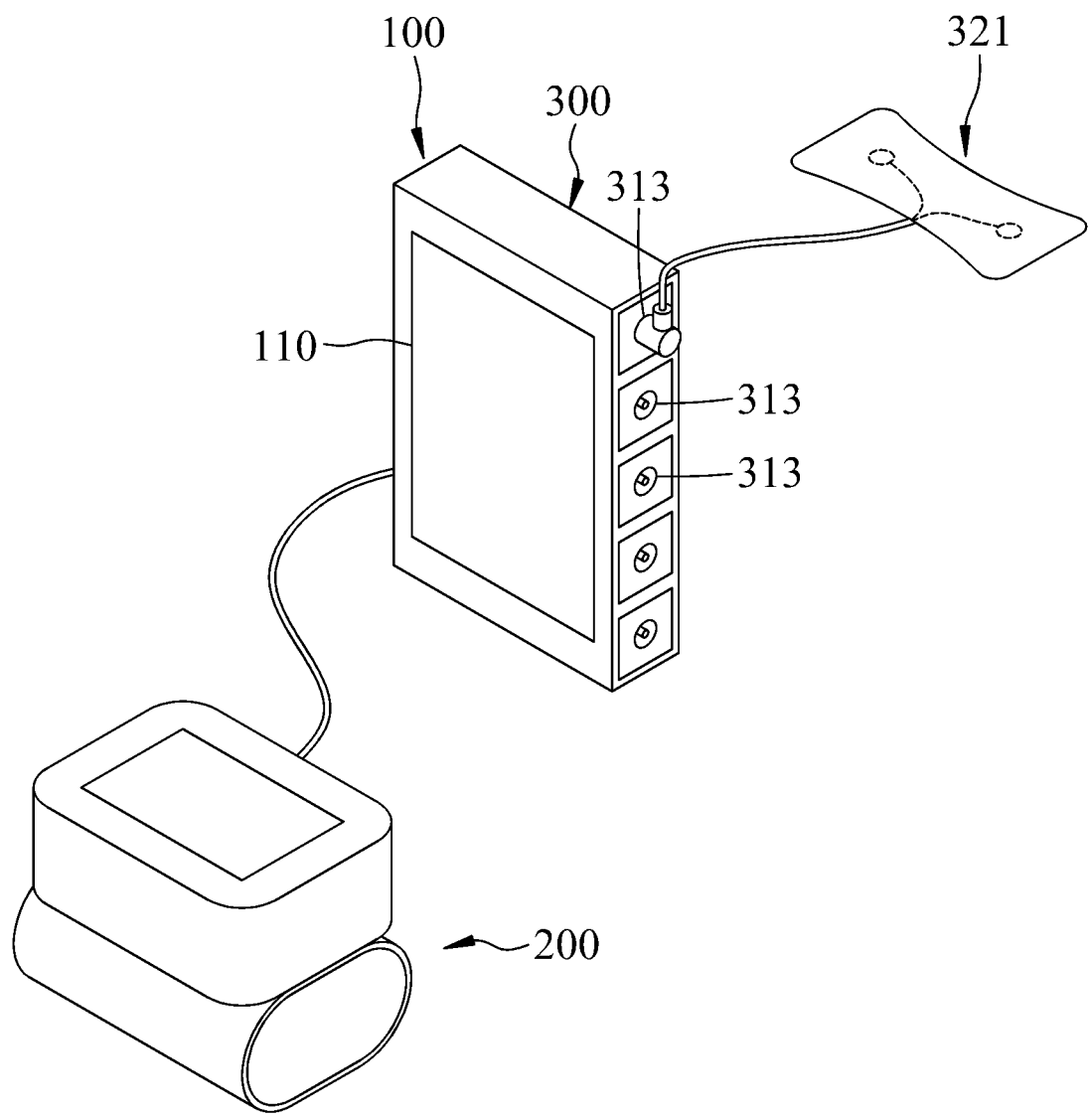
FIG. 4 is a perspective view illustrating another implementation of the embodiment, wherein the implementation includes a control device and a stimulation device that are integrated into a single electronic device, and an electrode pad unit that has a single pad with a pair of electrodes disposed thereon.

The electrode pad unit 321 can be used to introduce electric stimulation to stimulate the skin of the user 500 based on the stimulation spectrum. In one implementation, the electrode pad unit 321 may include a positive electrode pad and a negative electrode pad as shown in FIG. 1. In one implementation, the electrode pad unit 321 may include only one pad that has both the positive electrode and the negative electrode disposed thereon, as shown in FIG. 4. A weak current will flow from the positive electrode to the negative electrode through the contacted skin, subcutaneous tissue, and muscle, and a current loop is thus formed. The muscles under the stimulated skin will contract intermittently and resonate with relevant meridians, organs, and/or tissues. In addition to electricity, light, sound, and vibration are also forms of energy, so they can also be used to stimulate the human body.

In one implementation, the flashing device can be used as the stimulator 320 that emits flashing light to stimulate organs of the visual system or the skin of the user 500 based on the stimulation spectrum. The flashing device may include a lamp that is capable of reacting to a high-frequency signal, so as to emit flashing light based on the stimulation signal, triggering a limbic system of the brain to adjust physiological signals. The lamp may be installed in a room to serve as a lighting apparatus. The user 500 may wear an eye mask when sleeping, so as to continue being stimulated during sleep.

In one implementation, the acoustic frequency generator can be used as the stimulator 320 to output sound to stimulate acoustic organs or the skin of the user 500 based on the stimulation spectrum. Early in the "Huangdi Neijing" (or called "Inner Canon of the Yellow Emperor", an ancient Chinese medical text), relationships between the organs and the tones have been mentioned. In view of modern physics, this means to induce resonance in the organs via the frequencies of sounds, so as to adjust the conditions of the organs. Accordingly, the acoustic frequency generator may include a speaker that is capable of reacting to a high-frequency signal, so as to output sounds (regardless of whether it is in the hearing range of humans or not) based on the stimulation signal to stimulate organs of the auditory system or the skin. In addition to output sound of a single frequency, the acoustic frequency generator may use carrier waves to hide the stimulation signal in a melody, so the user 500 can imperceptibly receive the stimulation.

In one implementation, the vibrator or the body shaker can be used as the stimulator 320. An eccentric motor or the principles of magnetism may be adopted to realize the vibrator or the body shaker that requires a greater power to induce vibration. The vibrator or the body shaker can be integrated into objects that are frequently used in daily lives, such as a seat cushion, a mattress, gloves, socks, etc., facilitating accessibility of stimulation in daily lives so stimulation received by the user 500 can be prolonged. The stimulation generated by the vibrator or the body shaker may vibrate the skin of the user 500 or shake the limbs or the body of the user 500.

In this embodiment, the pulse generator 310 further includes a plurality of connectors 313 coupled to the pulse module 312, so multiple stimulators 320 of one or more types can be connected to the pulse generator 312 via the corresponding connectors 313. In practice, a switching circuit (not shown) may be used to switch connection of the pulse generator 312 to one or more desired stimulators 320 via the corresponding connectors 313. Accordingly, the user 500 may use multiple types of the stimulators 320 to receive multiple types of stimulations at the same time, or used multiple stimulators 320 of the same type to receive stimulations at multiple body parts at the same time.

The data unit 400 has built therein a database 410, a plurality of predetermined user operation modes 420, a plurality of predetermined pulse examination modes 430, and a spectrum database 440. Each of the predetermined user operation modes 420 corresponds to an individual symptom of poor circulation of qi and blood. In one embodiment, the user interface 110 is further configured to receive a symptom input related to a symptom of poor circulation of qi and blood, and the control device 100 outputs to the data unit 400 a symptom signal related to the symptom of poor circulation of qi and blood based on the symptom input. The data unit 400 is configured to retrieve from the database 410 a treatment direction (e.g., suggested setting for the parameters in the operation settings) corresponding to the symptom of poor circulation of qi and blood by operating in one of the predetermined user operation modes 420 that corresponds to the symptom of poor circulation of qi and blood to which the symptom signal is related, and to output the treatment direction (serving as the suggestion message) thus retrieved to the control device 100 for display by the user interface 110, so that the user 500 may perform stimulation according to the treatment direction for alleviating the symptom of poor circulation of qi and blood. In addition, the data unit 400 may receive from the pulse examination instrument 220 the result of the pulse examination (called examination data hereinafter), retrieve from the database 410 an analysis result related to improving the circulation of qi and blood by operating in one of the predetermined pulse examination modes 430 that corresponds to the examination data, and output the analysis result thus retrieved to the control device 100 for display by the user interface 110. The spectrum database 440 stores multiple spectrums which correspond to organs and tissues of a human body and each of which corresponds to a single frequency, and multiple spectrums which correspond to different types of medicines each inducing resonance of one or more specific meridians after being taken by a human being. The control device 100 is further configured to output the control signal to the data unit 400, and the data unit 400 is configured to output the organ-tissue-related spectrum and the medication-related spectrum to the pulse modulation module 311 based on the control signal. In other words, the modulation module 311 selects the organ-tissue-related spectrum from among the spectrums corresponding to organs and tissues, and selects the medication-related spectrum from among the spectrums corresponding to medicine types. The abovementioned decoupling results and the matrices corresponding to the weighting values are stored in the spectrum database 440 in this embodiment.

The control device 100 may be realized as a microcontroller, a desktop computer, a notebook computer, a tablet computer, a smart television, a smartphone, a smartwatch or any electronic device developed to implement the system according to this disclosure. The user interface 110 may be a display interface, such as a display screen. The data unit 400 may be a memory device (not shown) included in the control device 100, or a cloud storage system (not shown). Modern-day smartphones, smartwatches and the like are usually equipped with high-performance processors, multi-functional sensors, various apps (applications), and Internet accessibility. Such devices can acquire the suggestion message via the Internet or apps installed therein, and are suitable for implementing the control device 100, the pulse examining device 200 and the data unit 400 of this disclosure. Particularly, using the cloud storage system is convenient for management and/or analysis of user-related information, such as records of usage, illness-related search history, or examination data output by the pulse examination instrument 220, so as to provide personalized management of diagnosis data, prevent loss of data, and facilitate integration of relevant medical applications.

In summary, the embodiment of this disclosure generates the stimulation to stimulate the sensory system of the human body by integrating the meridian-related spectrum, the organ-tissue-related spectrum, and medication-related spectrum, and uses feedback control techniques to adjust the stimulation. Multiple types of stimulators 320 may provide different types of stimulations for the user 500, thereby improving circulation of qi and blood for the user 500.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A system for generating stimulations to stimulate a sensory system of a human body, said system comprising:
    a control device including:
        a user interface configured to provide options of medicines, options of meridians, options of organs, and options of tissue for a user to enter an operation input related to medicines, and meridians, organs and tissues of a human body by selecting one of the options of medicines, one of the options of meridians, one of the options of organs, and one of the options of tissue; and
        a control module configured to output a control signal based on the operation input;
    a pulse examining device configured to output a pulsation signal that is related to arterial pulsation of a user; and
    a stimulation device including:
        a pulse generator coupled to said control module and receiving the control signal therefrom, coupled to said pulse examining device and receiving the pulsation signal therefrom, and configured:
            to obtain a fundamental frequency for arteries of the user based on the pulsation signal;
            to obtain, based on the control signal, a meridian-related spectrum of a single frequency that corresponds to said one of the options of meridians selected by the user and that is a harmonic frequency of the fundamental frequency;
            to obtain, based on the control signal, an organ-tissue-related spectrum of a single frequency that corresponds to said one of the options of organs selected by the user and said one of the options of tissues selected by the user;
            to obtain, based on the control signal, a medication-related spectrum that corresponds to said one of the options of medicines selected by the user;
            to generate a stimulation spectrum by making a linear combination of the meridian-related spectrum, the organ-tissue-related spectrum and the medication-related spectrum; and
            to output a stimulation signal that has the stimulation spectrum; and
        a stimulator coupled to said pulse generator and receiving the stimulation signal therefrom, and configured to stimulate a sensory system of the user based on the stimulation spectrum.

2. The system of claim 1, wherein said stimulator includes one of an electrode pad unit configured to introduce electric stimulation to stimulate skin of the user based on the stimulation spectrum, a flashing device configured to emit flashing light to stimulate organs of a visual system or the skin of the user based on the stimulation spectrum, an acoustic frequency generator configured to output sound to stimulate organs of an auditory system or the skin of the user based on the stimulation spectrum, a vibrator configured to vibrate the skin of the user based on the stimulation spectrum, and a body shaker configured to shake limbs or a body of the user.

3. The system of claim 1, wherein said pulse generator includes a modulation module configured to record and analyze the pulsation signal to acquire a pulsation spectrum related to pulsations of the arteries of the user within a time interval; and
    wherein said control module is configured to receive the pulsation spectrum from said pulse generator, to determine, based on the pulsation spectrum, adjustments for weighting values used in the linear combination of the meridian-related spectrum, the organ-tissue-related spectrum and the medication-related spectrum in a real time manner, and to output the control signal that indicates the adjustments for the weighting values in a real time manner.

4. The system of claim 1, wherein said pulse examining device includes a pulse sensor configured to sense the arterial pulsation of the user, and to output the pulsation signal related to the arterial pulsation thus sensed;
    wherein said user interface is further configured to receive a pulse rate input that is manually inputted by the user and that is related to a user-determined pulse rate; and
    wherein said control module is further configured to output to said pulse generator a pulse rate signal related to the user-determined pulse rate; and
    wherein said pulse generator is further configured to obtain the fundamental frequency for arteries of the user based on the pulse rate signal.

5. The system of claim 1, further comprising a data unit that has an analysis database and a plurality of predetermined user operation modes built therein, each of said predetermined user operation modes corresponding to an individual symptom of poor circulation of qi and blood,
    wherein said user interface is further configured to receive a symptom input related to a symptom of poor circulation of qi and blood, and said control device is further configured to output to said data unit a symptom signal related to the symptom of poor circulation of qi and blood based on the symptom input; and
    wherein said data unit is configured to retrieve from said analysis database a treatment direction corresponding to the symptom of poor circulation of qi and blood by operating in one of said predetermined user operation modes that corresponds to the symptom of poor circulation of qi and blood to which the symptom signal is related, and to output the treatment direction thus retrieved to said control device for display by said user interface.

6. The system of claim 5, wherein said data unit is disposed to receive examination data, further has a plurality of predetermined pulse examination modes built therein, and is configured to retrieve from said analysis database an analysis result related to improving circulation of qi and blood by operating in one of said predetermined pulse examination modes that corresponds to the examination data, and to output the analysis result thus retrieved to said control device for display by said user interface.

7. The system of claim 6, further comprising a pulse examination instrument configured to perform pulse examination on the user, and to output to said data unit a result of the pulse examination thus performed to serve as the examination data.

8. The system of claim 5, wherein said data unit further includes a spectrum database that stores multiple spectrums which correspond to organs and tissues of a human body and each of which corresponds to a single frequency, and multiple spectrums which correspond to different medicine types;

wherein said control device is further configured to output the control signal to the data unit, and said data unit is configured to output the organ-tissue-related spectrum and the medication-related spectrum to said pulse generator based on the control signal;

wherein the organ-tissue-related spectrum is selected from among the spectrums corresponding to organs and tissues, and the medication-related spectrum is selected from among the spectrums corresponding to the different medicine types.

9. The system of claim 1, wherein said pulse generator is further configured to make, based on the control signal, the stimulation spectrum sequentially correspond to different linear combinations of the meridian-related spectrum, the organ-tissue-related spectrum and the medication-related spectrum respectively in different time intervals.

* * * * *